United States Patent
Peine

(10) Patent No.: US 12,167,901 B2
(45) Date of Patent: Dec. 17, 2024

(54) TELEMENTORING CONTROL ASSEMBLIES FOR ROBOTIC SURGICAL SYSTEMS

(71) Applicant: Covidien LP, Mansfield, MA (US)

(72) Inventor: William Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 1116 days.

(21) Appl. No.: 16/975,020

(22) PCT Filed: Mar. 18, 2019

(86) PCT No.: PCT/US2019/022671
§ 371 (c)(1),
(2) Date: Aug. 21, 2020

(87) PCT Pub. No.: WO2019/190792
PCT Pub. Date: Oct. 3, 2019

(65) Prior Publication Data
US 2021/0030499 A1    Feb. 4, 2021

Related U.S. Application Data

(60) Provisional application No. 62/647,998, filed on Mar. 26, 2018.

(51) Int. Cl.
*A61B 34/35* (2016.01)
*A61B 34/00* (2016.01)
*A61B 90/00* (2016.01)

(52) U.S. Cl.
CPC .............. *A61B 34/35* (2016.02); *A61B 34/74* (2016.02); *A61B 34/76* (2016.02); *A61B 90/361* (2016.02); *A61B 90/37* (2016.02); *A61B 2034/742* (2016.02); *A61B 2090/365* (2016.02); *A61B 2562/0257* (2013.01)

(58) Field of Classification Search
None
See application file for complete search history.

(56) References Cited

U.S. PATENT DOCUMENTS

| | | |
|---|---|---|
| 6,770,027 B2 | 8/2004 | Banik et al. |
| 7,158,860 B2 | 1/2007 | Wang et al. |
| 7,743,960 B2 | 6/2010 | Whitman et al. |
| 8,016,858 B2 | 9/2011 | Whitman |
| 8,073,528 B2 | 12/2011 | Zhao et al. |
| 8,517,243 B2 | 8/2013 | Giordano et al. |
| 8,965,583 B2 | 2/2015 | Ortmaier et al. |
| 9,107,698 B2 | 8/2015 | Razzaque et al. |

(Continued)

OTHER PUBLICATIONS

Partial Supplementary European Search Report dated Feb. 4, 2022 corresponding to counterpart Patent Application EP 19776788.2.

*Primary Examiner* — Patricia J Park
(74) *Attorney, Agent, or Firm* — Carter, DeLuca & Farrell LLP

(57) ABSTRACT

Methods and systems are provided for facilitating telementored surgical procedures. The systems include a portable input handle further including a housing, a position sensor disposed adjacent to the housing, and a position transmitter in communication with the position sensor. The position sensor may be configured to sense a pose of the housing relative to the position transmitter. The position transmitter may be configured to receive and transmit the sensed pose of the housing to the robotic surgical system.

19 Claims, 7 Drawing Sheets

(56) References Cited

U.S. PATENT DOCUMENTS

| | | | |
|---|---|---|---|
| 2007/0167702 A1 | 7/2007 | Hasser et al. | |
| 2008/0221591 A1* | 9/2008 | Farritor | A61B 34/70 |
| | | | 606/130 |
| 2009/0088775 A1* | 4/2009 | Swarup | A61B 34/71 |
| | | | 700/264 |
| 2010/0170519 A1* | 7/2010 | Romo | A61B 34/30 |
| | | | 606/130 |
| 2010/0228265 A1* | 9/2010 | Prisco | B25J 9/1689 |
| | | | 606/130 |
| 2010/0234857 A1* | 9/2010 | Itkowitz | G09B 23/285 |
| | | | 700/259 |
| 2011/0306986 A1 | 12/2011 | Lee et al. | |
| 2016/0081754 A1 | 3/2016 | Kostrzewski et al. | |
| 2016/0140875 A1 | 5/2016 | Kumar et al. | |
| 2016/0249992 A1* | 9/2016 | Ruiz Morales | A61B 17/00 |
| | | | 606/130 |
| 2016/0353055 A1 | 12/2016 | Popescu et al. | |
| 2017/0007255 A1* | 1/2017 | Jaworek | A61B 18/1445 |
| 2017/0071688 A1* | 3/2017 | Cohen | A61B 34/74 |
| 2017/0319282 A1 | 11/2017 | Jarc et al. | |
| 2018/0092706 A1* | 4/2018 | Anderson | A61B 34/74 |
| 2018/0297211 A1* | 10/2018 | Schaible | B25J 13/025 |
| 2019/0142531 A1* | 5/2019 | Wentworth | A61B 34/30 |
| | | | 606/130 |
| 2019/0175285 A1* | 6/2019 | Siemionow | A61B 34/10 |

* cited by examiner

TELEMENTORING CONTROL ASSEMBLIES FOR ROBOTIC SURGICAL SYSTEMS

CROSS-REFERENCE TO RELATED APPLICATIONS

This application is a U.S. National Stage Application filed under 35 U.S.C. § 371 (a) of International Patent Application Serial No. PCT/US2019/022671, filed Mar. 18, 2019, which claims the benefit of and priority to U.S. Provisional Patent Application Ser. No. 62/647,998, filed Mar. 26, 2018, the entire disclosure of which is incorporated by reference herein.

BACKGROUND

Robotic surgical systems have been developed for use in minimally invasive medical procedures. Typically, robotic surgical systems include a clinician console located remote from one or more robotic arms to which surgical instruments and/or cameras are coupled. For example, the clinician console may be located on another side of the operating room from the robotic arms, in another room, or in another building, and includes input handles and/or other input devices to be actuated by a clinician. Signals, based on the actuation of the input handles, are communicated to a central controller, which translates the signals into commands for manipulating the robotic arms and/or the surgical instruments coupled thereto, for example, within a surgical site. The controller, in turn, is often manipulated by a console which may be connected either via a wired connection or wireless connection.

When training a novice clinician to use the robotic surgical system, the novice clinician may stand over a master clinician who is positioned at a console remote from the robotic system while a patient is placed on a platform adjacent the robotic arms. The master clinician provides input to a clinician interface at the console to thereby control the robotic system, for example, by using input handles to manipulate a tool coupled to the robotic arm, such as an end effector or surgical instrument, to perform surgical operations on the patient. To provide the novice clinician with a full training experience, the expert surgeon may switch positions with the novice clinician to allow the novice clinician to deliver an input into the console.

Although hands-on experience is an important aspect of a well-rounded training program, providing access to such experience can be challenging for certain procedures. For example, time may be of the essence in some surgical procedures, and hence, having the novice clinician switch positions with the expert surgeon during the procedure may not be feasible. In other cases, certain steps of the procedure may not be handed off to another surgeon mid-procedure. As such, there is a need for improved systems and methods for training on robotic surgical systems.

SUMMARY

The present disclosure relates to robotic surgical systems and, more particularly, to systems and methods for controlling consoles included in a robotic surgical system.

The present disclosure relates to a robotic surgical system. The robotic surgical system includes a robotic arm coupled to a surgical tool, an imaging device configured to capture images of the surgical tool, a first console, a second console, a display, and a controller. The first console has a first input handle configured to receive an input to manipulate the robotic arm and the surgical tool. The second console has a second input handle configured to receive an input. The controller is coupled to the robotic arm, the imaging device, the first input handle, the second input handle, and the display. The controller causes the display to display captured images of the surgical tool. Additionally, the controller, in response to receiving the input at the second input handle, generates an image of a virtual surgical tool, and causes the display to display the image of the virtual surgical tool.

According to aspects of the present disclosure, the second input handle of the robotic surgical system includes a position sensor. The second console includes a position transmitter configured to receive pose data of the position sensor relative to the position transmitter and to transmit the pose data to the controller. The controller causes the display to display the image of the virtual surgical tool on the display at a location in a displayed surgical site corresponding to the pose data of the position sensor.

In another aspect of the present disclosure, the second input handle may include a proximity sensor configured to detect an object and, in response to a detection of an absence of the object, the controller may cause the display not to display the images of the surgical tool.

In another aspect of the present disclosure the second console may include a remote controller in communication with the controller, and the second input handle may be in wired communication with the remote controller.

In still another aspect, the second console includes a remote controller in communication with the controller, and the second input handle is wirelessly coupled to the remote controller.

According to an aspect, the second input handle includes a first input button configured to receive an input, and in response to the received input, the controller may cause energization of the surgical tool.

In another aspect, the second input handle includes a vibration device coupled to the controller, and the vibration device is configured to vibrate in response to a detected movement of the second input handle In aspects of the present disclosure, a portable handle system for use in a robotic surgical system is provided. The portable input handle system includes a portable input handle with a housing and a position sensor disposed adjacent to the housing. A position transmitter may be included which is in communication with the position sensor. The position sensor may sense a pose of the housing relative to the position transmitter, the position transmitter configured to receive and transmit the sensed pose of the housing to the robotic surgical system.

According to aspects, the portable input handle may further include a proximity sensor configured to detect a presence of an object adjacent thereto.

In accordance with certain aspects, the portable input handle system may further include a vibration device disposed in the housing and configured to vibrate in response to a predetermined sensed pose of the housing.

In yet another aspect, the housing of the portable input handle defines a cavity. The portable input handle may further include a microcontroller, a gripper motor, and a vibration device disposed in the cavity, the microcontroller coupled to the gripper motor and the vibration device.

In another aspect, the portable input handle may include an input button in communication with the gripper motor, the input button configured to selectively engage and disengage from the gripper motor.

According to another aspect, the portable input handle may be wirelessly coupled to the position transmitter.

In another aspect, the portable input handle may be coupled to the position transmitter by a tether.

In still another aspect, a shroud is disposed over at least the portable input handle.

According to aspects of the present disclosure, a method of operating a telementoring robotic surgical system is provided, the robotic surgical system including a first console having a first display, a second console including a second display and a portable input handle, and a robotic arm including a surgical tool coupled to a controller in communication with the first console and the second console. The method may include capturing images of a surgical site using an imaging device, and displaying the image on a first display and a second display. An input at the portable input handle may be detected. In response to detecting the input at the portable input handle, an image of a virtual surgical tool may be generated, and the image of the virtual surgical tool may be displayed on the first display and the second display.

In another aspect, the display of images on the first display and the second display may include capturing of the surgical tool in the surgical site and displaying the images of the surgical tool on the first display. The method may further include receiving a pose of the portable input handle. The image of the virtual surgical tool may be generated. The generated image of the virtual surgical tool may be displayed on the captured images of the surgical site at corresponding locations in the surgical site based on the received pose of the portable input handle.

According to yet another aspect, input may be received indicating movement of the portable input handle from a first pose to a second pose. In response to the received input, the image of the virtual surgical tool may be updated.

According to aspects, the method may further include detecting an object located at a distance less than a predetermined value from the portable input handle. In response to the distance detected being less than a predetermined value, continuing to display the image of the virtual surgical tool. Alternatively, in response to the distance being greater than the predetermined value discontinuing the display of the image of the virtual surgical tool.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF THE DRAWINGS

Figure 1:
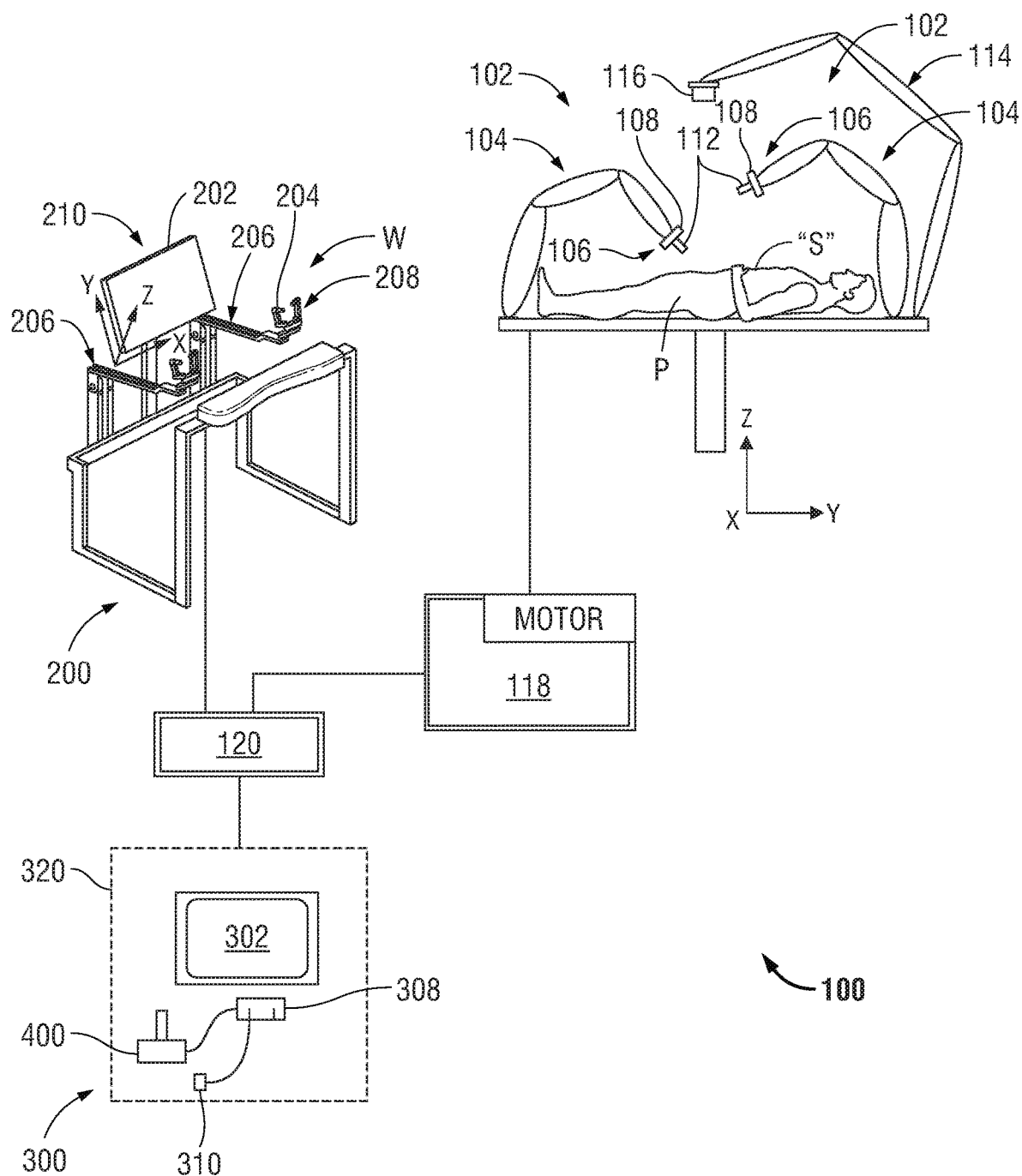
FIG. 1 is a schematic illustration of a robotic surgical system including a robot system, a first clinician interface having two control arm assemblies, and a second clinician interface having a portable input handle, in accordance with an embodiment of the present disclosure.

Embodiments of the present disclosure are described in detail with reference to the drawings, in which like reference numerals designate identical or corresponding elements in each of the several views. As used herein, the term "distal" refers to the portion of the component being described which is closer to a patient, while the term "proximal" refers to the portion of the component being described which is further from the patient. The term "clinician" as used herein refers to a doctor, nurse, healthcare provider which may include support personnel, or other operators of the surgical system described. The term "surgical field" as used herein refers to the space in which the robotic surgical system operates. Such space may include, but is not limited to, an operating room, robot storage and maintenance facility, or other space in which the surgical robot is disposed for mechanical operation.

Referring to FIG. 1, a multi-input robotic surgical system 100 in accordance with the present disclosure is shown generally and includes a surgical robotic system 102, a controller 120, and consoles 200, 300. The surgical robotic system 102 generally includes robotic arms 104 and a tower 118. Each of the robotic arms 104, which may be in the form of linkages, has an end 106 that moveably supports an end effector, instrument or surgical tool 112 configured to act on tissue. The ends 106 of the robotic arms 104 may include an imaging device 108 for imaging a surgical site "S".

Each console 200, 300 communicates with the tower 118 through the controller 120 and includes a display 202, 302 which is configured to display images. In accordance with an embodiment, the displays 202, 302 display three-dimensional images of the surgical site "S" which may include imaging data captured by imaging devices 108 and/or include imaging data captured by imaging devices (not shown) that are positioned about the surgical theater (e.g., an imaging device positioned within the surgical site "S"), an imaging device positioned adjacent the patient "P", or an imaging device 116 positioned at a distal end of an imaging arm 114). The imaging devices (e.g., imaging devices 108, 116) may capture visual images, infra-red images, ultrasound images, X-ray images, thermal images, and/or any other known real-time images of the surgical site "S". The imaging devices 108, 116 transmit captured imaging data to the controller 120 which creates three-dimensional images of the surgical site "S" in real-time from the imaging data and transmits the three-dimensional images to the displays 202, 302 for display. In another embodiment, the displayed images are two-dimensional renderings of the data captured by the imaging devices.

According to an embodiment of the present disclosure, clinician interface 200 has a console configuration, for example, as illustrated in FIG. 1. In this embodiment, console 200 defines a workspace "W" and includes input handles 204 attached to gimbals 208 which allow a surgeon to manipulate the surgical robotic system 102 (e.g., move the robotic arms 104, the ends 106 of the robotic arms 104, and/or the surgical tools 112). Each of the gimbals 208 is in communication with the controller 120 to transmit control signals thereto and to receive feedback signals therefrom. Additionally or alternatively, each of the gimbals 208 may include control interfaces or input handles 204 which allow the surgeon to manipulate (e.g., clamp, grasp, fire, open, close, rotate, thrust, slice, etc.) the surgical tools 112 supported at the ends 106 of the robotic arms 104.

Each of the gimbals 208 is moveable to move the ends 106 of the robotic arms 104 and/or to manipulate surgical tools 112 within a surgical site "S". The three-dimensional images on the display 202 are orientated such that movement of the gimbals 208 moves the ends 106 of the robotic arms 104 and/or the tools 112 as viewed on the displays 202, 302. It will be appreciated that the orientation of the three-dimensional images on the display device may be mirrored or rotated relative to view from above the patient "P". In addition, it will be appreciated that the size of the three-dimensional images on the displays 202, 302 may be scaled to be larger or smaller than the actual structures of the surgical site "S" permitting the surgeon to have a better view of structures within the surgical site "S". As the gimbal 208 is moved, the surgical tools 112 are moved within the surgical site "S". Movement of the surgical tools 112 may also include movement of the ends 106 of the robotic arms 104 which support the surgical tools 112. Although illustrated as a handle, input handle 204 may further include a handle including a clutch switch, touchpad, joystick, keyboard, mouse, or other computer accessory, and/or a foot switch, pedal, trackball, or other actuatable device configured to translate physical movement from the clinician to signals sent to the controller 120.

The control arm 206 is rotatable about six axes of rotation and translation in response to a surgeon interfacing with the gimbal 208 (e.g., interfacing with input handle 204 disposed on an input shaft (not shown)). Input handle 204 may include one or more buttons or paddles (not shown) used to control an end effector of surgical tool 112, such as to open or close grasping members, and may thus provide a seventh axis of rotation and translation. Movement of the control arm 206 about the six axes of rotation is detected by the controller 120 (see FIG. 1) to manipulate the robotic arms 104 and surgical tools 112 of the multi-input robotic surgical system 100. The construction of the control arm 206 and gimbal 208 allows movement of the respective members and arms to rotation about the six axes of rotation.

The movement of the surgical tools 112 are scaled relative to the movement of the input handles 204, and hence, the control arm 206 and gimbals 208. When the input handles 204 are moved within a predefined workspace "W", the input handles 204 send control signals to the controller 120. The controller 120 analyzes the control signals to move the surgical tools 112 in response to the control signals. The controller 120 transmits scaled control signals to the tower 118 to move the surgical tools 112 in response the movement of the input handles 204.

Figure 2:
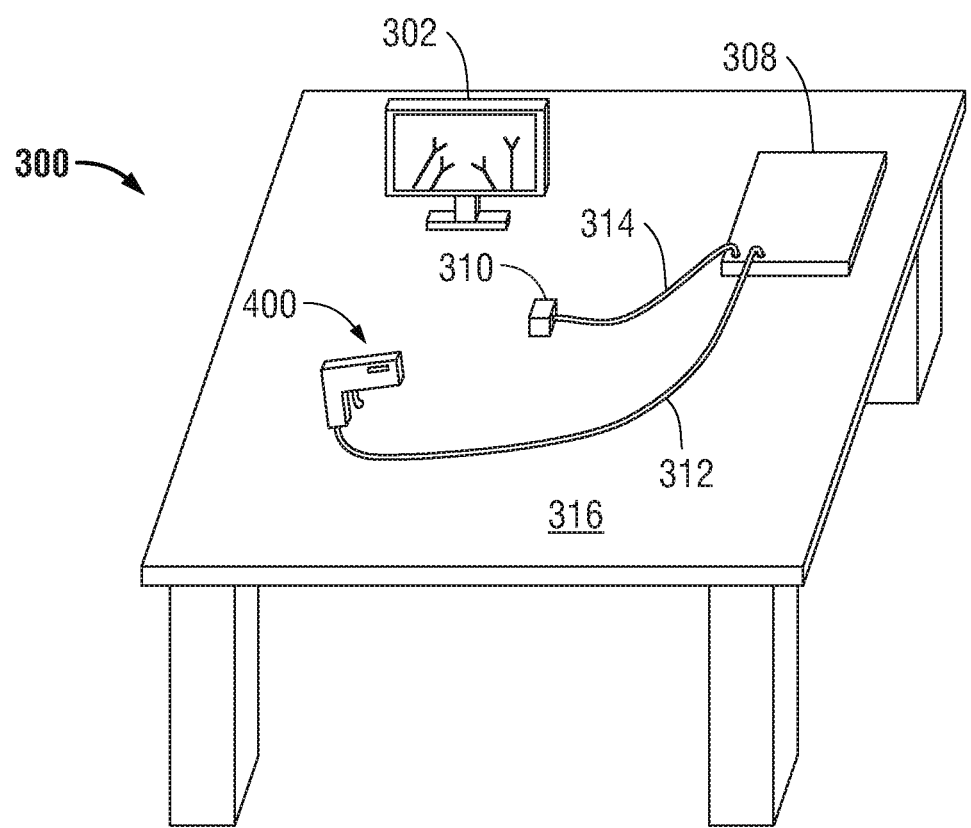
FIG. 2 is a perspective view of the second clinician interface of FIG. 1.

According to another embodiment, clinician interface 300 has a portable configuration and is configured as a remote manipulation system. With additional reference to FIG. 2, in this regard, the console 300 includes a display 302, similar to display 202, a portable input handle 400, a position transmitter 310, and a computer 308. The portable input handle 400 is configured to be transportable to permit the clinician to manipulate the multi-input robotic surgical system 100 (e.g., move the robotic arms 104, the ends 106 of the robotic arms 104, and/or the surgical tools 112) without being confined to a particular location. In this regard, the portable input handle 400 is in communication with the computer 308 to transmit control signals thereto and to receive feedback signals therefrom. As shown in FIG. 2, the portable input handle 400 is tethered to a computer 308 via a cable 312. The cable 312 may be a multi-conductor electrical cable which provides power and communication lines for the portable input handle 400. In other embodiments, the portable input handle 400 is wirelessly coupled to the computer 308.

Figure 3:
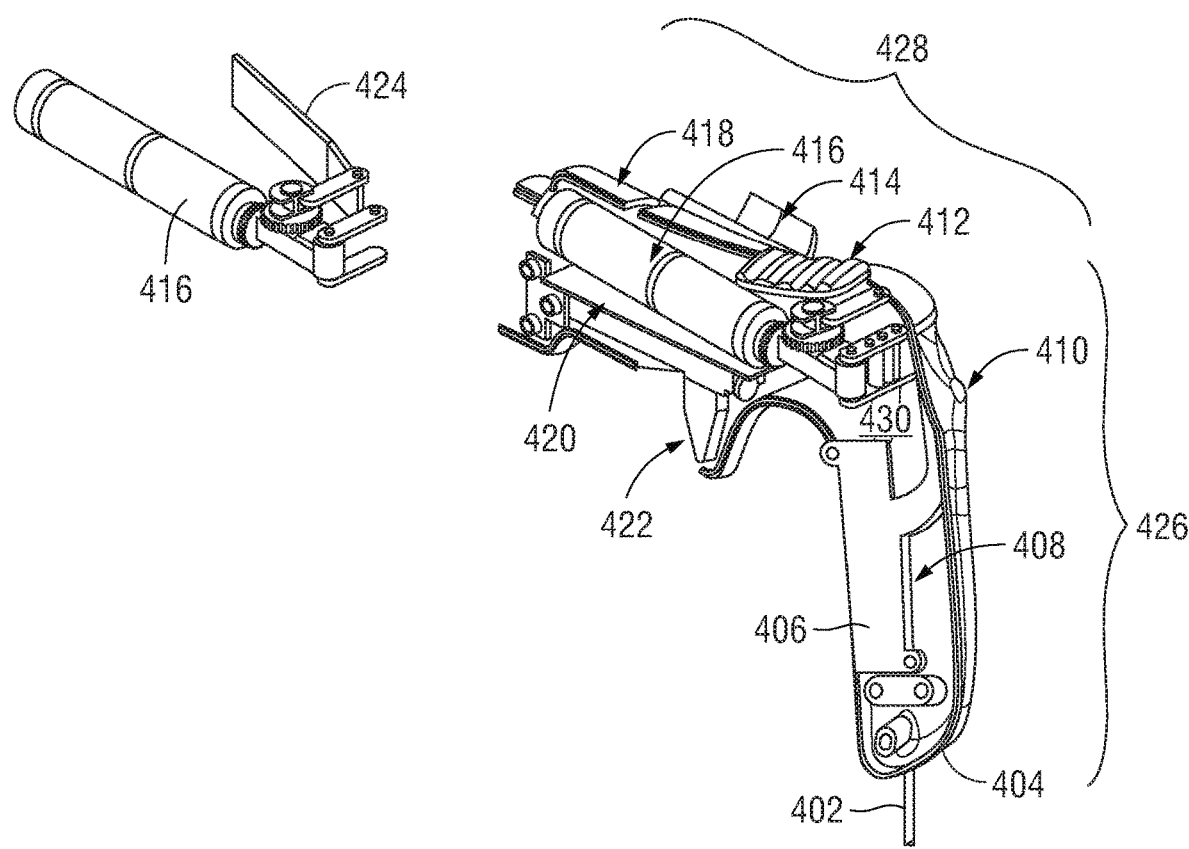
FIG. 3 is a perspective view of a portable input handle of FIG. 1.

Referring now to FIG. 3, the portable input handle 400 generally includes a housing 404 (only one half of which is shown), input buttons 422, 412, 424, a microcontroller 420, handle electronics 406, a gripper motor 416, and sensors 410, 414. In addition to containing the components of the portable input handle 400, the housing 404 is configured to be gripped by a clinician and includes a handle portion 426 and a body 428 extending from the handle portion 426. The housing 404 is generally made of a durable, lightweight material, such as plastic and may be designed as a clamshell, which when assembled together forms a cavity 430 for the disposal of the components of the portable input handle 400. Although generally having a smooth surface, the handle portion 426 is configured to rest in the palm of the clinician and may have a rough or tacky outer surface for easier grasping.

The body 428 of the housing 404 includes various openings through which the input buttons 412, 422, 424 are accessible or may extend. The input buttons 412, 422, 424 are provided to permit the clinician to selectively energize or manipulate the surgical tool 112. In an embodiment, input button 412, 422, 424 are electrically coupled to microcontroller 420 so that the clinician may selectively provide an input which is transmitted to the controller 120 to cause energization of the surgical tool 112. For comfort and ease of access, input button 422 may be spaced apart from the handle portion 426 so as to be actuatable by the clinician's index finger. For example, input button may be in the form of a trigger, which when actuated, causes energization of the surgical tool 112.

Input button 412 may be provided near input button 422, for example, on a top side of the body 428 which would be most accessible by the clinician's thumb while still gripping handle portion 426. When actuated by a clinician, input button 412 places the gripper motor 416 in a pose control mode (e.g. a "clutching" mode), and when released, re-engages with the gripper motor 416. That is, when input button 412 is actuated, the surgical tool 112 and/or robotic arm 104 controlled by the portable input handle 400 stop tracking the motion of the portable input handle 400, thereby allowing the clinician to manipulate or reposition the portable input handle 400 without affecting the pose of the surgical tool 112 and/or robotic arm 104. In an embodiment, the clutching and/or re-engagement of gripper motor 416 is transmitted to robotic arm 104, to provide signals thereto for the manipulation of robotic arm 104 and/or surgical tool 112. For example, if the clinician grips the portable input handle 400 to rotate the surgical tool 112 during stitching, the clinician may need to rotate his or her hand between an initial pose and a final pose several times to cause the surgical tool 112 to form a single stitch. As such, the clinician may then need to return his or her hand to the initial pose during the stitching, and hence, prior to the rotation of the clinician's hand back to the first pose, the clinician may actuate input button 412 to place the gripper motor 416 in a pose control mode to thereby clutch the motors controlling the surgical tool 112 and then release the input button 412 to re-engage the same motors. As used herein, the term "pose"

refers to a position and an orientation of an object, for example, the position and orientation of the surgical tool 112.

Input button 424 may be provided adjacent the input button 412, for example, on a side of the body 428 which would be easy accessible by the clinician's index finger while the clinician's hand grips handle portion 426. In response to actuation of input button 424, an electric signal is sent to microcontroller 420 which, in turn, records the positional movement of input button 424 and transmits the recorded movement to the controller 120. The controller 120 then transmits a control signal to the robotic arm 104 to correspondingly move the surgical tool 112. Generally, actuation of input button 424 corresponds to a similar actuation (e.g., opening/closing) of surgical tool 112.

As a safety measure, portable input handle 400 includes sensor 410, which is configured to detect an object, such as the clinician's hand, and to provide feedback signals of the detection to microcontroller 420. For example, sensor 410 may be any one of numerous types of sensors suitable for detecting proximity of an object, such as an infrared sensor, inductive sensor, magnetic sensor, or other such suitable sensor. Upon receipt of a signal that an object, such as the clinician's hand, is not within proximity of sensor 410 (for example, a distance of the object is above a threshold value), microcontroller 420 may transmit signals to controller 120, which may prevent or stop display of a virtual surgical tool on the displays 202, 304 or present or stop movement of the robotic arm 104, if necessary.

With continued reference to FIG. 3, the portable input handle 400 may include one or more light-emitting diodes (LEDs) 418 to indicate to the clinician the portable input handle 400 state, multi-input robotic surgical system 100 state, or surgical robotic system 102 state. For example, the LEDs 418 may emit light in a variety of colors to indicate a current state or mode of operation of one or more of the portable input handle 400, the multi-input robotic surgical system 100, and/or the robotic surgical system 102. To allow the clinician increased freedom in the manipulation of the portable input handle 400, sensor 414 operates with position transmitter 310 so that sensor 414 detects the pose of the portable input handle 400 through a three dimensional field, and the sensed pose of the portable input handle 400 is transmitted by the position transmitter 310 to controller 120. Transmission of pose data associated with the portable input handle 400 may occur at a specific time or, alternatively, continuously as a stream of data. According to an embodiment, sensor 414 may be a 6-axis remote position sensor, such as an electromagnetic sensor, where the pose of sensor 414 is tracked and then transmitted by position transmitter 310.

Figure 8:
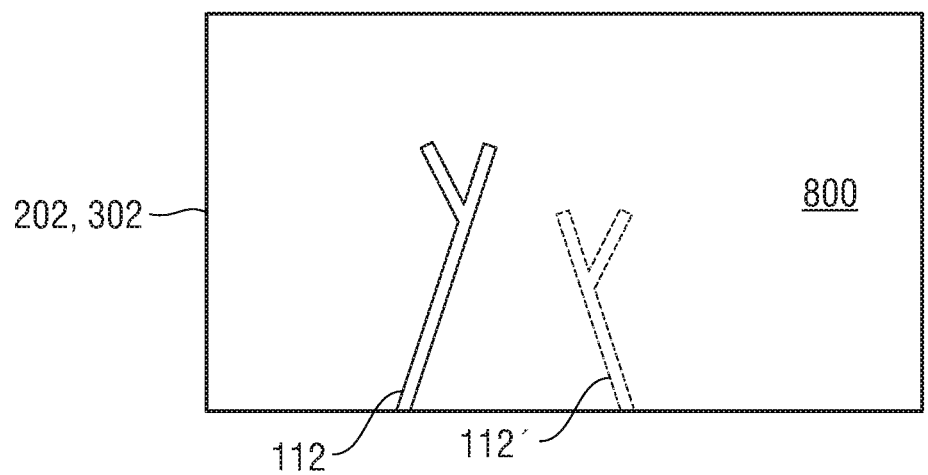
FIG. 8 is a screen shot of yet another step of the ghost telementoring process depicted in FIG. 5, in accordance with an embodiment of the present disclosure.
Figure 9:
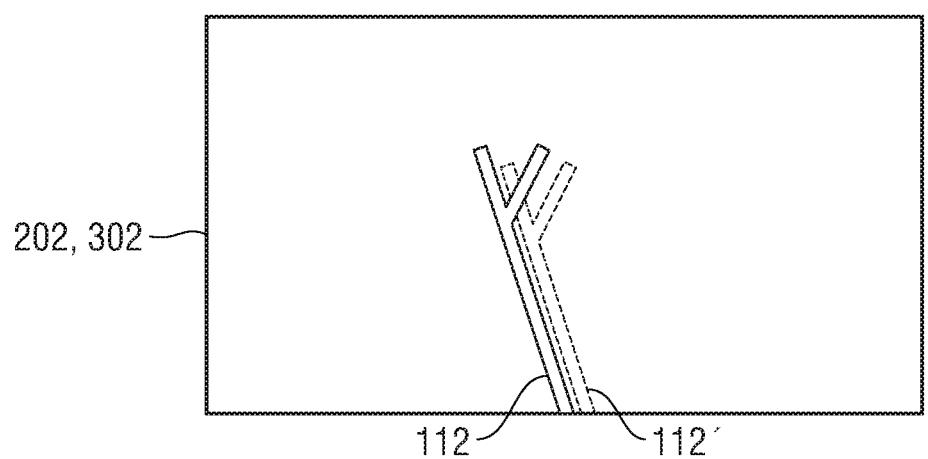
FIG. 9 is a screen shot of still another step of the ghost telementoring process depicted in FIG. 5, in accordance with an embodiment of the present disclosure.

The pose of sensor 414 may be tracked relative to the position transmitter 310 electromagnetically or optically. In another embodiment, one or more cameras (not shown) are included to capture images of the portable input handle 400 and/or console 300 where the computer 308 receives and processes the captured images using machine vision algorithms to measure the XYZ position and roll-pitch-yaw orientation of the portable input handle 400 relative to the position transmitter 310. Those skilled in the art will appreciate that these pose tracking techniques may be used individually or in combination without departing from the scope of the present disclosure. No matter the particular implementation, the input handles 204 and gimbals 208 of the console 200 are replaced with sensor 414 and position transmitter 310 to track the pose of the input handles 204 and permit the surgeon to manipulate (e.g., clamp, grasp, fire, open, close, rotate, thrust, slice, etc.) the surgical tools 112 supported at the ends 106 of the robotic arms 104. In an embodiment, the position transmitter 310 may transmit the sensed data as electric signals to the computer 308, and in turn, the computer 308 may transmit the electric signals to the controller 120 to reposition the surgical tool 112. The transmitted pose data may be used to display a virtual surgical tool 112' (see FIGS. 7-9) on one or both of the displays 202, 302 in a corresponding pose.

A vibration device 408 may be included in the handle portion 426 of the portable input handle 400. The vibration device 408 communicates with the computer 308, which provides signals to the microcontroller 420 to cause the vibration device 408 to vibrate in response to particular movements made by the clinician. As a result, the vibration device 408 provides a tactile sensation to the clinician when the portable input handle 400 is in use.

Returning to FIG. 2, position transmitter 310 and computer 308 may be located on a table 316, both to provide a level, fixed surface to locate the position transmitter 310 on as well as allow the clinician to relax or reposition themselves as necessary to prevent fatigue. It is contemplated that the portable input handle 400 may rest on a portable armrest (not shown), which may be removably attached to the table 316 to facilitate interaction between the position transmitter 310 and portable input handle 400. The armrest provides a similar feel and ergonomic benefit as the armrest in the console 200 and also defines the allowed workspace of the position tracker. The portable armrest may be clamped or hooked onto a tabletop or attached to a portable stand.

The display 302 may be located on the table 316 to receive images of the surgical tool 112 from imaging device 108, 116 located in a surgical field "S" or images of a virtual surgical tool 112'. Though embodiments described include a representation of the surgical tool 112, as well as the virtual surgical tool 112', it is contemplated that the display 202, 302 may also illustrate a cursor or other icon in the place of the virtual robotic surgical tool on the displays 202, 302 for a clinician to identify certain points of interest in a surgical field "S".

It is contemplated that, in certain embodiments, the table 402 may be located within an operation room. For example, with reference to FIG. 1, optionally, portable input handle 400 is illustrated as part of a sterile portable input handle system 318, which includes a shroud 320 dimensioned to cover at least a portion of the console 300, for example, over the portable input handle 400, to allow for a sterile interface to the operating surgeon and for protection from contact with contaminants. The shroud 320 permits the portable input handle 400 to be used in the operating room where patient "P" is located so that the clinician monitoring the surgical procedure may be scrubbed in to take over a surgical procedure if intervention becomes necessary.

Figure 4:
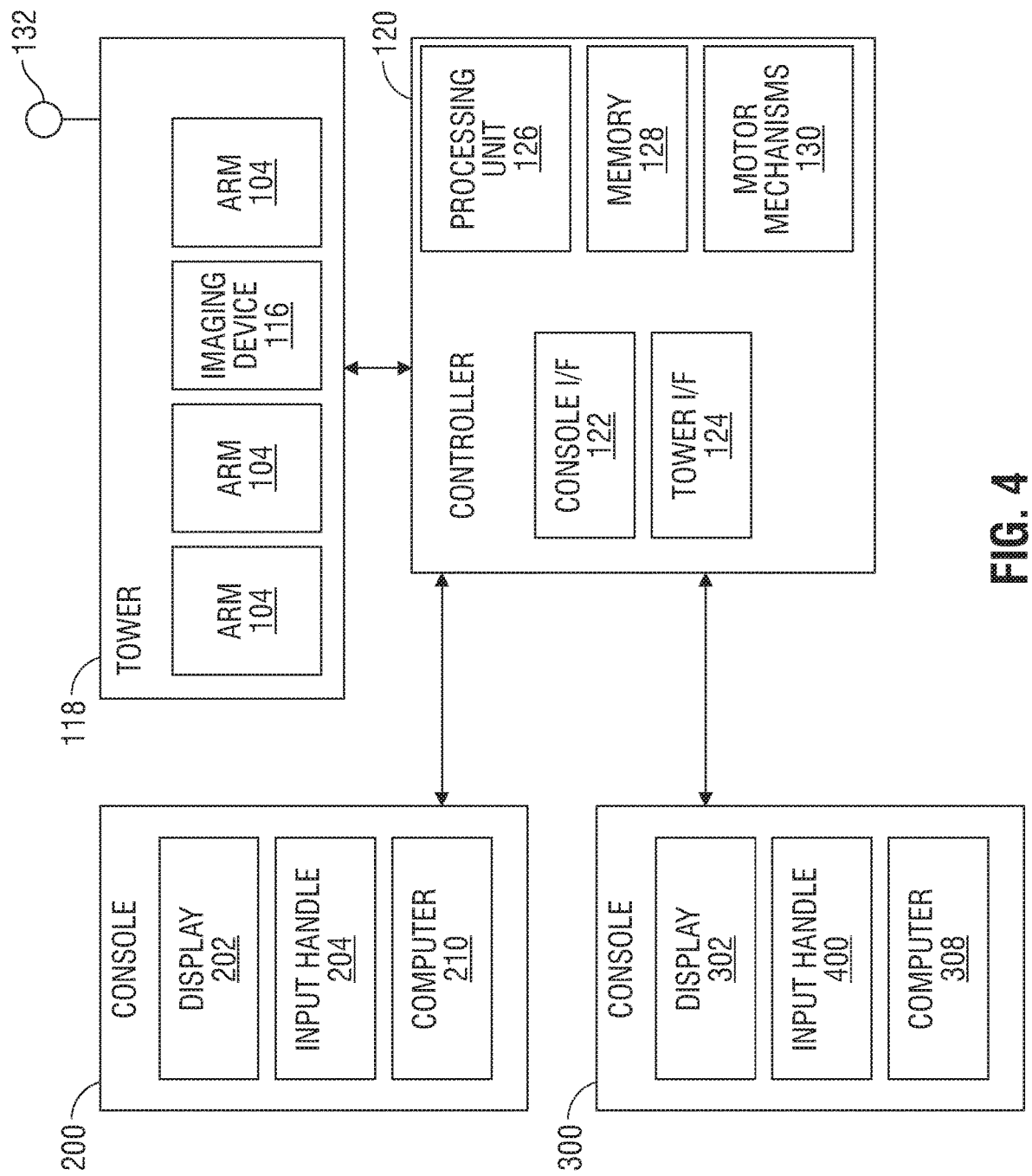
FIG. 4 is a functional block diagram of the multi-input robotic surgical system of FIG. 1.

FIG. 4 is a functional block diagram of the multi-input robotic surgical system 100 of FIG. 1. As noted above, the controller 120 is configured to communicate with the tower 118 to thereby provide instructions for operation, in response to input received from one of the consoles 200, 300. While FIG. 4 shows two consoles 200, 300, it will be appreciated that one of these consoles 200, 300 may be replaced by the portable input handle 400 and/or the portable input handle 400 may be used in addition to the consoles 200, 300. In some embodiments, the portable input handle 400 may form part of console 300. In this regard, the controller 120 generally includes a processing unit 126, a memory 128, a tower interface 124, and a consoles interface 122. The processing unit 126, in particular by means of a computer program stored in the memory 128, functions in such a way to cause components of the tower 118 to execute a desired movement according to a movement defined by input handle 204 of the console 200. The processing unit 126 includes any suitable logic control circuit adapted to perform calculations and/or operate according to a set of instructions. The processing unit 126 may include one or more processing devices, such as a microprocessor-type of processing device or other physical device capable of executing instructions stored in the memory 128 and/or processing data. The memory 128 may include transitory type memory (e.g., RAM) and/or non-transitory type memory (e.g., flash media, disk media, etc.). The tower interface 124 and consoles interface 122 communicate with the tower 118 and console 200 and, in an embodiment, which console 300, respectively, either wirelessly (e.g., Wi-Fi, Bluetooth, LTE, etc.) and/or via wired configurations. Although depicted as separate modules, the console interface 122 and tower interface 124 are a single component in other embodiments.

The tower 118 includes a communications interface 132 configured to receive communications and/or data from the tower interface 124 for manipulating motor mechanisms to thereby move the robotic arms 104. In accordance with an embodiment, the motor mechanisms are configured to, in response to instructions from the processing unit 126, receive an application of current for mechanical manipulation of cables (not shown) which are attached to the robotic arms 104 to cause a desired movement of a selected one of the robotic arms 104 and/or surgical tool 112 coupled to the robotic arm 104. The tower 118 also includes imaging device 116, which captures real-time images and transmits data representing the images to the controller 120 via the communications interface 132.

To manipulate the surgical tools 112 associated with the tower 118, each console 200, 300 has display 202, 302, and a computer 210, 308. As noted above, the first console 200 and second console 300 have input handle 204 and/or portable input handle 400 attached, respectively. Both the input handle 204 and portable input handle 400 couple to corresponding computers 210, 308 and are used by the clinician to transmit input to a controller 120. The input handle 204 associated with console 200 is removably attached to the gimbals 208 and is movable about the six axes of freedom which the gimbals 208 are capable of moving about. It is contemplated that the input handle 204 associated with the console 200 may be a handle, a pedal, or a computer accessory such as a keyboard, joystick, mouse, button, wheel, touch screen, switch, trackball or other similar component. For example, one or more buttons or other user input interfaces may be used to control the type of virtual surgical tool 112' being displayed. Additional buttons or other user input interfaces may be used to control the size at which the virtual surgical tool 112' is displayed. One or more buttons or other user input interfaces may also be used to mark reference positions, such as waypoints, of the virtual surgical tool 112' as it is positioned within the surgical site "S". Likewise, one or more buttons or other user input interfaces may be used to allow the clinician to provide visual guidance, such as by drawing lines or shapes, etc., that is displayed along with the virtual surgical tool 112'. One or more buttons or pedals may also be used to allow the clinician to indicate when an end effector of the surgical tool 112 represented by the virtual surgical tool 112' should be activated, such as by energizing the surgical tool 112 or activating a stapling or clipping function, etc. The indication of the activation of the end effector may be represented by a change in color of the displayed virtual surgical tool 112' and/or by audible, textual, or other graphical instruction.

The displays 202, 302 display images or other data received from the controller 120 to thereby communicate the data to the clinician. The computers 210, 308 associated with the first console 200 and second console 300, respectively, include a processing unit and memory, which further include data, instructions and/or information related to the various components, algorithms, and/or operations of the tower 118 and can operate using any suitable electronic service, database, platform, cloud, or the like.

Figure 5:
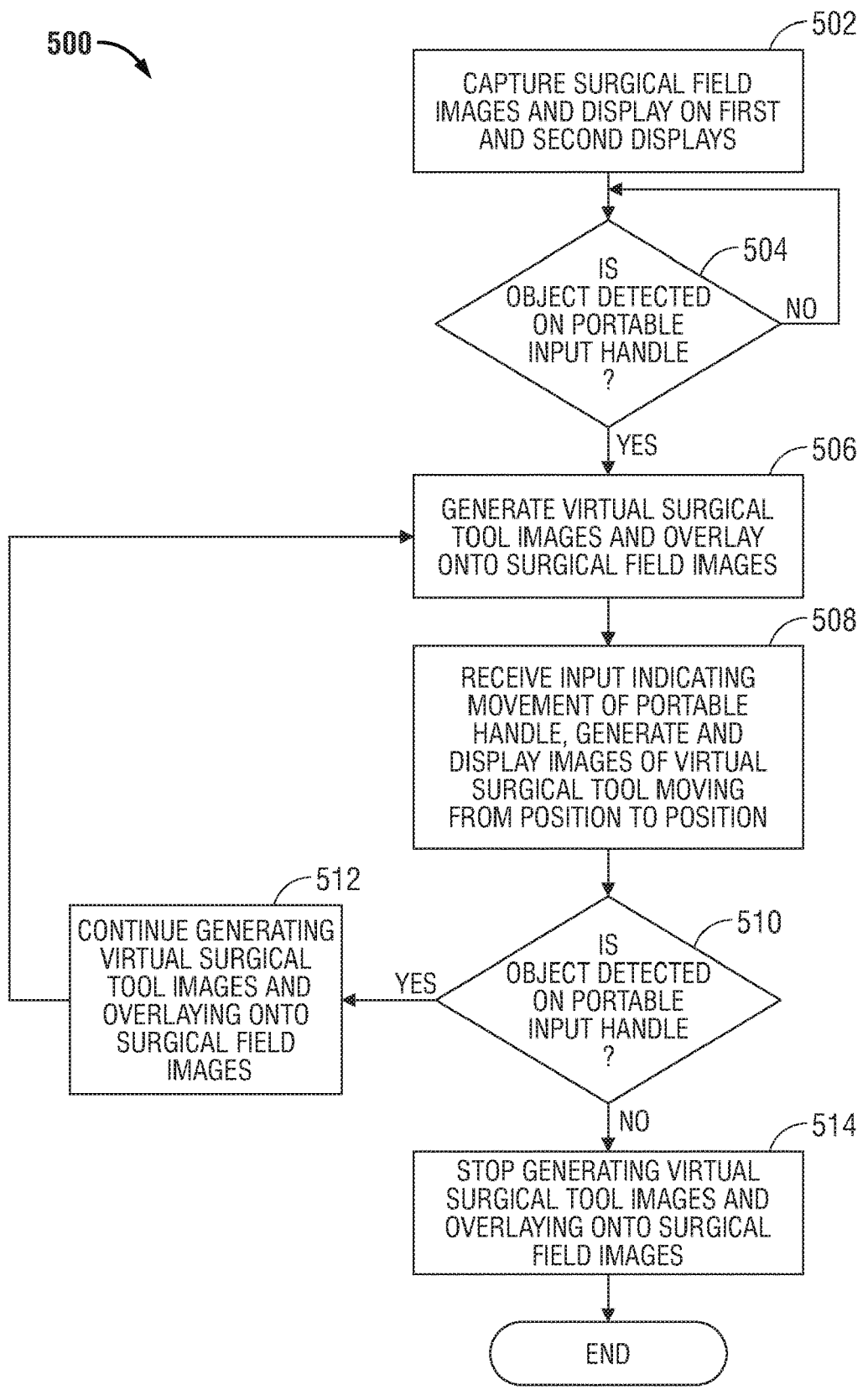
FIG. 5 is a flow diagram of a ghost telementoring process, in accordance with an embodiment of the present disclosure.

With reference to FIG. 5, illustrated is a ghost telementoring process 500 (hereinafter "process 500") in which controller 120 may, upon receiving inputs from at least two consoles 200, 300, display an image of the surgical robotic system and an image of a virtual surgical tool 112' overlaid onto the image of the surgical robotic system. As noted above, in some embodiments one of consoles 200, 300 may be replaced by the portable input handle 400, or, in the alternative, portable input handle 400 may form part of console 300. Specifically, as a first clinician manipulates the surgical robotic system 102 from the first console, a second clinician manipulates a virtual surgical robotic system from the second console. While the first clinician and second provide inputs, respectively, the controller 120 displays the surgical robotic system 102 and an overlaid virtual surgical robotic system simultaneously on both displays 202, 302.

Figure 6:
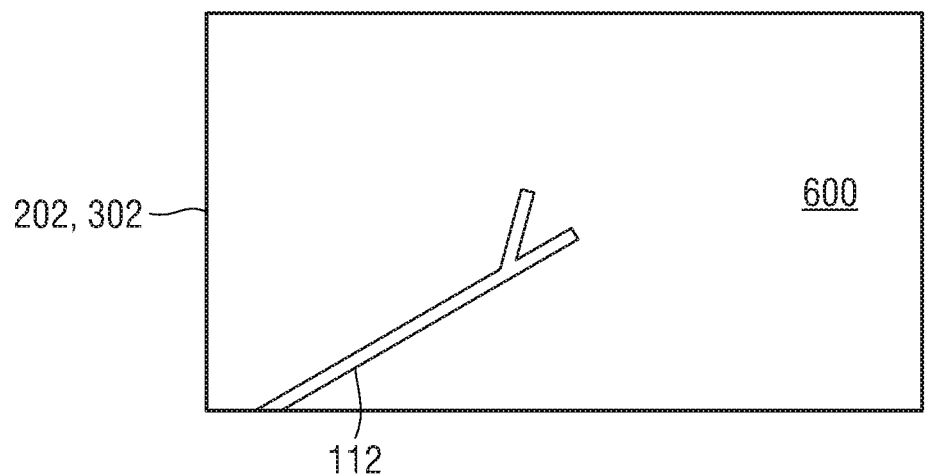
FIG. 6 is a screen shot of a step of the ghost telementoring process depicted in FIG. 5, in accordance with an embodiment of the present disclosure.

With further reference to FIG. 5, in this regard, at step 502, images of the surgical field "S", which may include surgical tool 112, are captured by the imaging device 108 and transmitted by the controller 120 to the displays 202, 302 for display. In an embodiment, images captured of the surgical tool 112 while the surgical tool 112 is disposed in a first pose may be displayed on the displays 202, 302 to provide clinicians at both consoles 200, 300 a view of the location of the surgical tool 112 relative to the surgical site "S". A display 600 according to an embodiment is illustrated in FIG. 6 and includes a captured image of surgical tool 112.

At some point during the surgical procedure, an input may be received at the first console 200 to reposition the surgical tool 112. For example, the first clinician may provide an input to move the input handle 204 attached to the gimbal 208 from a first pose to a second pose to thereby move the surgical tool 112 from a first pose to a second pose. As the imaging device 108 continues to capture images of the surgical site "S", the updated images captured by the imaging device 108 are displayed on the displays 202, 302 to show the surgical tool 112 as it moves from the first pose to the second pose.

At step 504, a determination is made as to whether an object, such as the second clinician's hand, is detected on the portable input handle 400. For example, sensor 410 may detect an object and, if the distance of the object is below a predetermined value, a determination is made that the object is detected.

Figure 7:
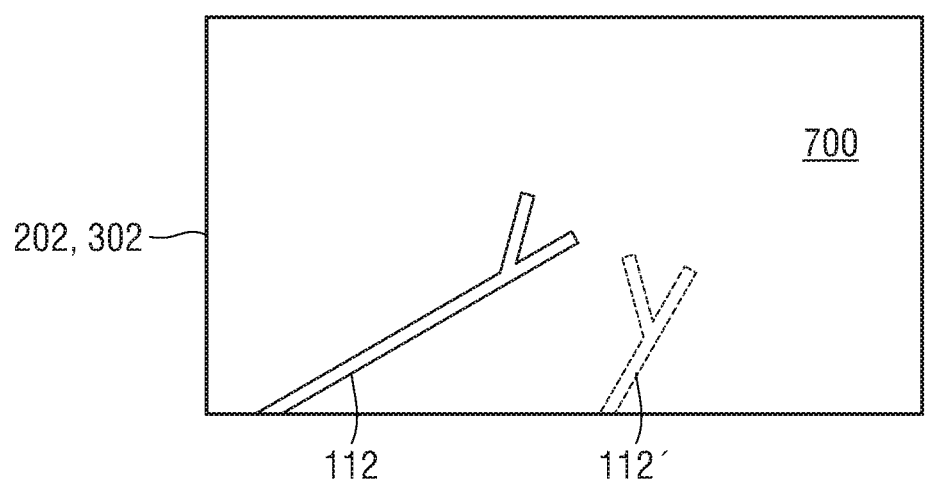
FIG. 7 is a screen shot of another step of the ghost telementoring process depicted in FIG. 5, in accordance with an embodiment of the present disclosure.

At step 506, in response to the detection of the object and/or based on input from the second clinician, images of a virtual surgical tool 112' are generated and overlaid onto the images of the surgical field "S" and/or surgical tool 112, displayed on the displays 202, 302. The images of the virtual surgical tool 112' may include three-dimensional images showing a depth as well as a pose of the virtual surgical tool 112', such as by showing the pose of the jaws of the virtual surgical tool 112' relative to the surgical site "S". Data related to the pose of the portable input handle 400 are provided to the controller 120, which uses the data to generate images of the virtual surgical tool 112' at a corresponding pose in the surgical site "S". The generated images are then displayed as an overlay on images of the surgical tool 112 on both displays 202, 302. A display 700 according an embodiment is illustrated in FIG. 7 and includes the captured image of surgical tool 112 and a virtual surgical tool 112'. While FIG. 7 shows a distal portion of the surgical tool 112 and the virtual surgical tool 112', those skilled in the art will recognize that additional portions of the surgical tool 112, the virtual surgical tool 112', and/or the surgical robotic system 102 may be shown based on the scale of the displayed images relative to the surgical tool 112 and virtual surgical tool 112'. Returning to step 504, if the object is not detected (for example, the distance of the object is above the predetermined value), the process 500 reiterates at block 504 or terminates.

In an embodiment, the second clinician may have a desire to indicate to the first clinician where to place surgical tool 112 in the surgical site "S". As such, the second clinician may move the virtual surgical tool 112' to a desired location so that the first clinician can follow the movement. In this regard, after step 506 at step 508, an input from the second console 300 of the portable input handle 400 may be received indicating movement of the portable input handle 400 from a first pose to a second pose, and in response, images are generated to display the virtual surgical tool 112' at a location in the surgical site "S" that corresponds to the movement from the first pose to the second pose. For example, as shown in display 800 of FIG. 8, the virtual surgical tool 112' has moved to a different position as compared with FIG. 7, which allows the second clinician to reposition surgical tool 112 as shown in display 900 of FIG. 9.

At block 510, a determination is made as to whether an object, such as the second clinician's hand, is detected on the portable input handle 400. For example, sensor 410 may detect an object and, if the distance of the object is below a predetermined value, a determination is made that the object is detected. In such case, the image of the virtual surgical tool 112' continues to be displayed overlaid on the displays 202, 302 at step 512, and process 500 reiterates at block 506. If the object is not detected (for example, the proximity distance of the object is above the predetermined value), the virtual surgical tool 112' is not displayed over the image of the surgical tool 112 is displayed on the displays 202, 302 at step 514, and the process 500 reiterates at block 504 or terminates.

The present disclosure provides novel systems, methods, and arrangements to assist master clinicians in teaching novice clinicians how to perform robotic surgical operations. One advantage of the disclosed systems and methods is the ability of instructor clinicians to provide instruction and/or guidance to other clinicians over great distances. For example, the disclosed systems and methods allows the instructor clinician to be in the same room as the other clinicians, or at some remote location connected to the training location via a network. Since the instructor clinician is not directly controlling the surgical robotic system, time delays caused by network connections do not cause safety concerns. Another advantage of the disclosed systems and methods is the ability of the instructor clinician to provide three-dimensional visual guidance of the movement and placement of surgical tools relative to a patient's anatomy. Though detailed descriptions of one or more embodiments of the disclosed technology have been provided for illustrative purposes, various alternatives, modifications, and equivalents will be apparent to those of ordinary skill in the art without varying or departing from the spirit of the invention. For example, while the embodiments described above refer to particular features, components, or combinations thereof, such features, components, and combinations may be substituted with functionally equivalent substitutes which may or may not contain the elements as originally described.

Further, while the disclosed embodiments contemplate location of a controller external to a robotic surgical system, it is contemplated that the controller may be located within the robotic surgical system, or alternatively that robotic surgical system components may include circuitry which executes the described force measurements and calculations independent of a controller.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A robotic surgical system, comprising:
a robotic arm coupled to a surgical tool;
an imaging device configured to capture images of the surgical tool and a surgical site;
a first console comprising a first input handle configured to receive an input to manipulate the robotic arm and the surgical tool;
a second console comprising a second input handle configured to receive an input to manipulate a virtual surgical tool;
a portable input handle comprising a housing, a first position sensor disposed adjacent the housing, a first proximity sensor disposed adjacent the housing, at least one camera configured to capture images of the portable input handle, and a computer;
a first position transmitter in communication with the first position sensor;
a display; and
a controller coupled to the robotic arm, the imaging device, the first input handle, the second input handle, the portable input handle, and the display,
wherein the controller causes the display to display the captured images of the surgical tool and the surgical site, and in response to receiving the input at the second input handle, generates an image of the virtual surgical tool and causes the display to display the image of the virtual surgical tool simultaneously with the image of the surgical tool and display the image of the virtual surgical tool as an overlay on the displayed image of the surgical site,
wherein the first position sensor is configured to sense a pose of the housing relative to the first position transmitter, and the first position transmitter is configured to receive and transmit the sensed pose of the housing to the robotic surgical system, the pose tracked optically relative to the first position sensor, and
wherein the computer is configured to process the captured images of the portable input handle using a machine vision algorithm to measure position and orientation data of the portable input handle relative to the first position transmitter.

2. The robotic surgical system of claim 1, wherein:
the second input handle comprises a second position sensor,
the second console further comprises a second position transmitter configured to receive pose data of the second position sensor relative to the second position transmitter and to transmit the pose data to the controller,
the controller causes the display to display the image of the virtual surgical tool on the display at a location in the displayed image of the surgical site corresponding to the pose data of the second position sensor,
wherein the second console includes a second proximity sensor configured to detect an object, and in response to a detection of an absence of the object in proximity to the second console, the controller causes the display not to display the image of the virtual surgical tool.

3. The robotic surgical system of claim 1, wherein the second console includes a remote controller in communication with the controller, and the second input handle is in wired communication with the remote controller.

4. The robotic surgical system of claim 1, wherein the second console includes a remote controller in communication with the controller, and the second input handle is wirelessly coupled to the remote controller.

5. The robotic surgical system of claim 1, wherein the second input handle comprises a first input button configured to receive an input, and in response to the received input, the controller causes energization of the surgical tool.

6. The robotic surgical system of claim 1, wherein the second input handle comprises a vibration device coupled to the controller, and the vibration device is configured to vibrate in response to a detected movement of the second input handle.

7. The robotic surgical system of claim 1, wherein the first console further comprises:
a gimbal affixed to the first input handle; and
a control arm configured to rotate about six axes of rotation and translation in response to a surgeon interfacing with the gimbal.

8. A portable input handle system for use in a robotic surgical system, comprising:
a portable input handle comprising a housing, a position sensor disposed adjacent the housing, a proximity sensor disposed adjacent the housing, at least one camera configured to capture images of the portable input handle, and a computer;
a controller coupled to the portable input handle and configured to generate an image of a virtual surgical tool on a display as an overlay on a displayed image of a surgical site; and
a position transmitter in communication with the position sensor,
wherein the position sensor is configured to sense a pose of the housing relative to the position transmitter, and the position transmitter is configured to receive and transmit the sensed pose of the housing to the robotic surgical system, the pose tracked optically relative to the position sensor,
wherein the proximity sensor is configured to detect a presence of an object adjacent thereto and, in response to a detection of an absence of the object, the controller causes the display not to display the image of the virtual surgical tool on the displayed image of the surgical site, and
wherein the computer is configured to process the captured images using a machine vision algorithm to measure position and orientation data of the portable input handle relative to the position transmitter.

9. The portable input handle system of claim 8, wherein the portable input handle further comprises a vibration device disposed in the housing and configured to vibrate in response to a predetermined sensed pose of the housing.

10. The portable input handle system of claim 8, wherein the housing of the portable input handle defines a cavity, the portable input handle further comprises a microcontroller, a gripper motor, and a vibration device disposed in the cavity, the microcontroller is coupled to the gripper motor and the vibration device.

11. The portable input handle system of claim 10, wherein the portable input handle includes an input button in communication with the gripper motor, the input button configured to selectively engage and disengage from the gripper motor.

12. The portable input handle system of claim 10, wherein the portable input handle is wirelessly coupled to the position transmitter.

13. The portable input handle system of claim 10, wherein the portable input handle is coupled to the position transmitter by a tether.

14. The portable input handle system of claim 8, wherein the position sensor is a 6-axis remote position sensor.

15. The portable input handle system of claim 11, wherein the input button is disposed on a top side of a body of the housing, the portable input handle system further comprising:
a second input button spaced apart from a handle portion of the portable input handle and disposed adjacent to the input button, the second input button comprising a trigger configured to energize a surgical tool;
a third input button disposed on a side of the body of the housing and adjacent to the input button, the third input button configured to actuate the surgical tool; and
a light-emitting diode configured to indicate a state of at least one of the portable input handle or the robotic surgical system.

16. A method of operating a telementoring robotic surgical system comprising a first console including a first display, a second console including a second display, and a portable input handle comprising a housing, a position sensor disposed adjacent the housing, a proximity sensor disposed adjacent the housing, at least one imaging device configured to capture images of the portable input handle, and a computer, a position transmitter in communication with the position sensor, and a robotic arm including a surgical tool coupled to a controller in communication with the first console and the second console, the method comprising:
capturing images of the portable input handle, the surgical tool, and a surgical site using the imaging device;
sensing a pose of the housing relative to the position transmitter using the position sensor;
receiving and transmitting the sensed pose of the housing to the telementoring robotic surgical system using the position transmitter, wherein the pose is tracked optically relative to the position sensor;
processing the captured images of the portable input handle using a machine vision algorithm to measure position and orientation data of the portable input handle relative to the position transmitter;
displaying the captured images of the surgical tool and the surgical site on the first display and the second display;
detecting an input at the portable input handle;
in response to detecting the input at the portable input handle, generating an image of a virtual surgical tool; and displaying the image of the virtual surgical tool simultaneously with the image of the surgical tool on the first display and displaying the image of the virtual surgical tool as an overlay on the displayed image of the surgical site.

17. The method of claim 16, wherein:

displaying the images on the first display and the second display includes capturing images of the surgical tool in the surgical site and displaying the images of the surgical tool on the first display and the second display, and the method further comprises:

receiving a pose of the portable input handle;

generating the image of the virtual surgical tool; and displaying the generated image of the virtual surgical tool on the captured images of the surgical site at a corresponding location in the surgical site based on the received pose of the portable input handle.

18. The method of claim 16, further comprising:

receiving an input indicating a movement of the portable input handle from a first pose to a second pose; and updating the image of the virtual surgical tool, in response to the received input.

19. The method of claim 16, further comprising:

detecting an object located at a distance greater than a predetermined value from the portable input handle, wherein:

in response to the distance being less than the predetermined value, continuing to display the image of the virtual surgical tool, and in response to the distance being greater than the predetermined value, discontinuing the display of the image of the virtual surgical tool.

* * * * *